US00PP36350P2

(12) United States Plant Patent
Amezquita

(10) Patent No.: US PP36,350 P2
(45) Date of Patent: Dec. 31, 2024

(54) ***HOYA* PLANT NAMED 'AMZ001'**

(50) Latin Name: *Hoya elliptica*
Varietal Denomination: AMZ001

(71) Applicant: Melody Amezquita, Southwest Ranches, FL (US)

(72) Inventor: Melody Amezquita, Southwest Ranches, FL (US)

( * ) Notice: Subject to any disclaimer, the term of this patent is extended or adjusted under 35 U.S.C. 154(b) by 0 days.

(21) Appl. No.: 18/445,977

(22) Filed: Apr. 23, 2024

(51) Int. Cl.
*A01H 6/08* (2018.01)
*A01H 5/12* (2018.01)

(52) U.S. Cl.
USPC ..... Plt./380

(58) Field of Classification Search
USPC ..... Plt./373, 380
See application file for complete search history.

(56) References Cited

U.S. PATENT DOCUMENTS

PP35,955 P2 * 7/2024 Xiangang ..... A01H 6/08 Plt./380
PP36,085 P2 * 8/2024 Xiangang ..... A01H 6/08 Plt./380

* cited by examiner

*Primary Examiner* — Karen M Redden
(74) *Attorney, Agent, or Firm* — Samuel R. McCoy

(57) ABSTRACT

A new and distinct *Hoya elliptica* plant named 'AMZ001' which is characterized by a vining habit, shortened internodal spacing, variegated foliage that is pale yellow-green in the central zone, occasionally blotched with a darker shade of yellow-green towards the marginal zone, and broadly margined with dark green, and the stability of these characteristics from generation to generation.

3 Drawing Sheets

Latin name of the genus and species: The Latin name of the genus and species of the novel variety disclosed herein is *Hoya elliptica.*

Variety denomination: The inventive variety of *Hoya* disclosed herein has been given the variety denomination 'AMZ001'.

BACKGROUND OF THE INVENTION

Parentage: The new plant originated as a spontaneous, partial-plant, branch mutation. The branch mutation was discovered at a greenhouse in Southwest Ranches, Florida, in March of 2022, growing amongst a plurality of cultivated unnamed *Hoya elliptica* plants (not patented). The mutation exhibited conspicuously variegated foliage relative to the parent. The mutation was isolated and grown to a mature size in order to evaluate stability and uniqueness of the characteristics first observed. Upon confirmation of the stability and uniqueness, the new plant was selected for commercialization and given the name, 'AMZ001'.

Asexual Reproduction: Asexual reproduction of the new cultivar 'AMZ001', by way of softwood stem cuttings, was first initiated in July of 2022 in Southwest Ranches, Florida. Approximately twenty-five plants, propagated across multiple generations have shown that the unique features of the instant cultivar are stable and reproduced true to type.

SUMMARY OF THE INVENTION

The cultivar 'AMZ001' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMZ001'. These characteristics in combination distinguish 'AMZ001' as a new and distinct *Hoya* cultivar:

1. *Hoya* 'AMZ001' exhibits a vining habit with an abundance of fleshy, elliptic foliage arranged oppositely along the entire length of the scandent stems and lateral branches; and
2. *Hoya* 'AMZ001' exhibits shortened internodal spacing; and
3. *Hoya* 'AMZ001' exhibits variegated foliage that is a pale yellow-green coloration in the central zone of the lamina, occasionally blotched with a darker shade of yellow-green towards the marginal zone, and broadly margined with dark green; and
4. *Hoya* 'AMZ001' exhibits axillary umbels bearing an abundance of small white flowers with red-purple centers; and
5. *Hoya* 'AMZ001' exhibits a slower rate of growth relative to the parent and species.

BOTANICAL DESCRIPTION OF THE PLANT

Figure 1:
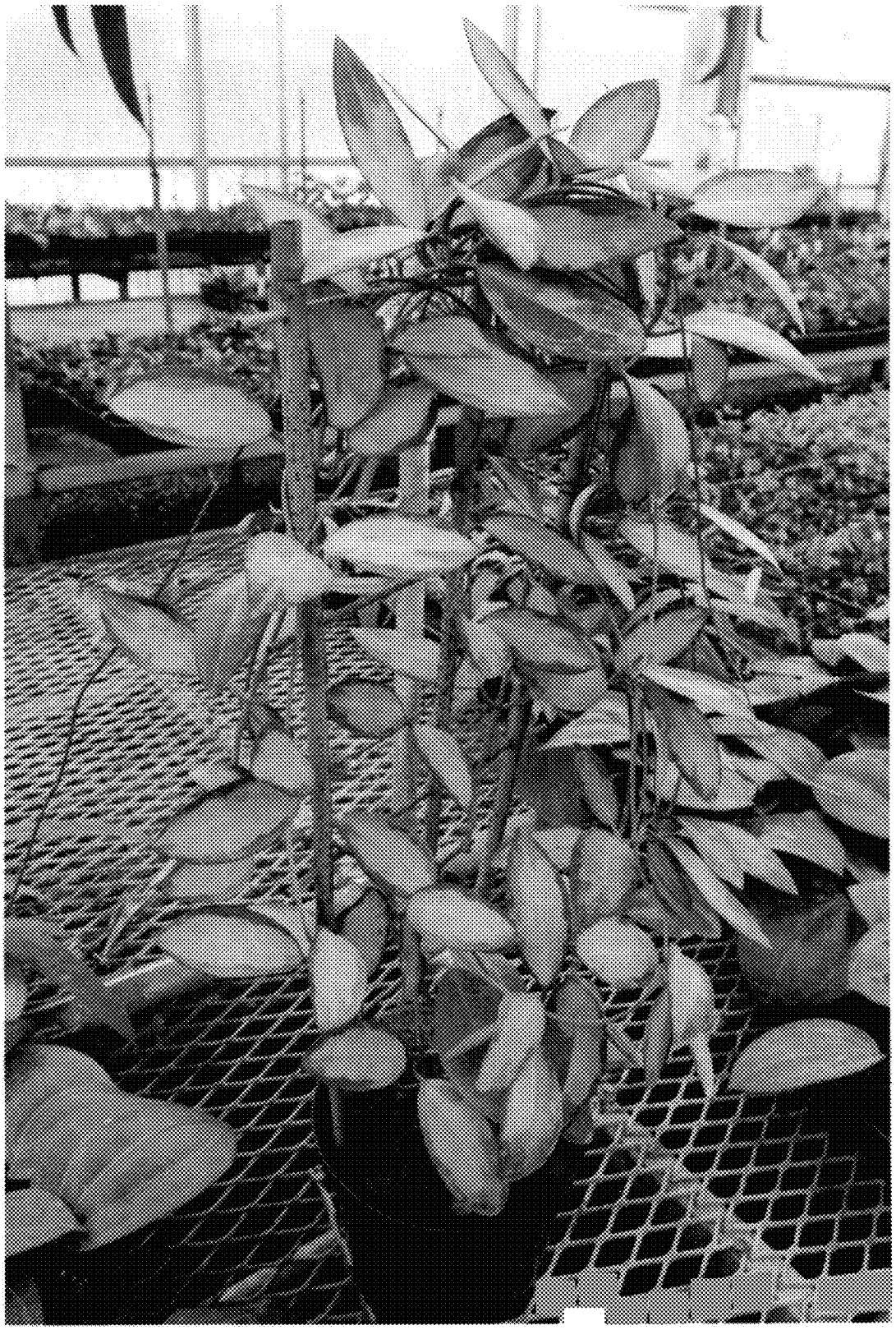
FIG. 1 illustrates, as nearly true as it is reasonably possible to make the same in color photographs of this type, an exemplary 2-year-old 'AMZ001' plant in a 14 cm nursery pot in a greenhouse in Southwest Ranches, Florida.
Figure 2:
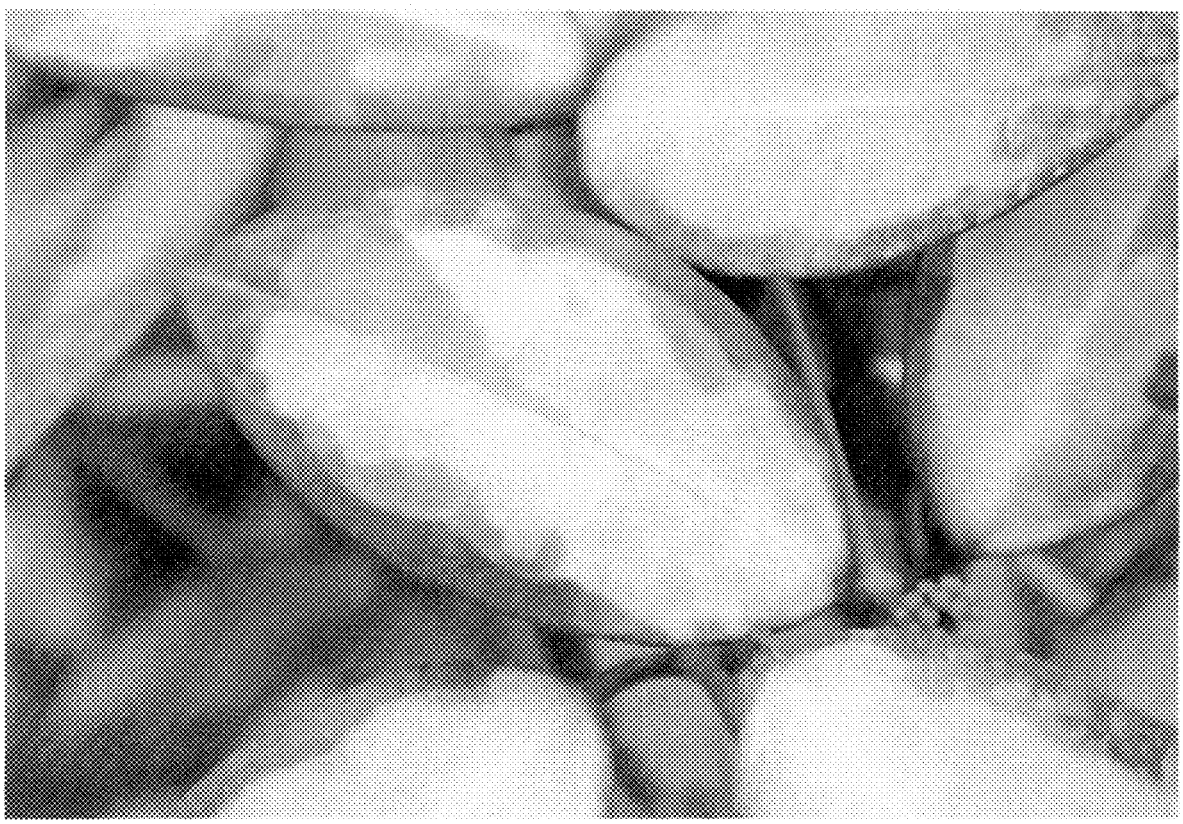
FIG. 2 illustrates, as nearly true as it is reasonably possible to make the same in color photographs of this type, the mature foliage of 'AMZ001'.
Figure 3:
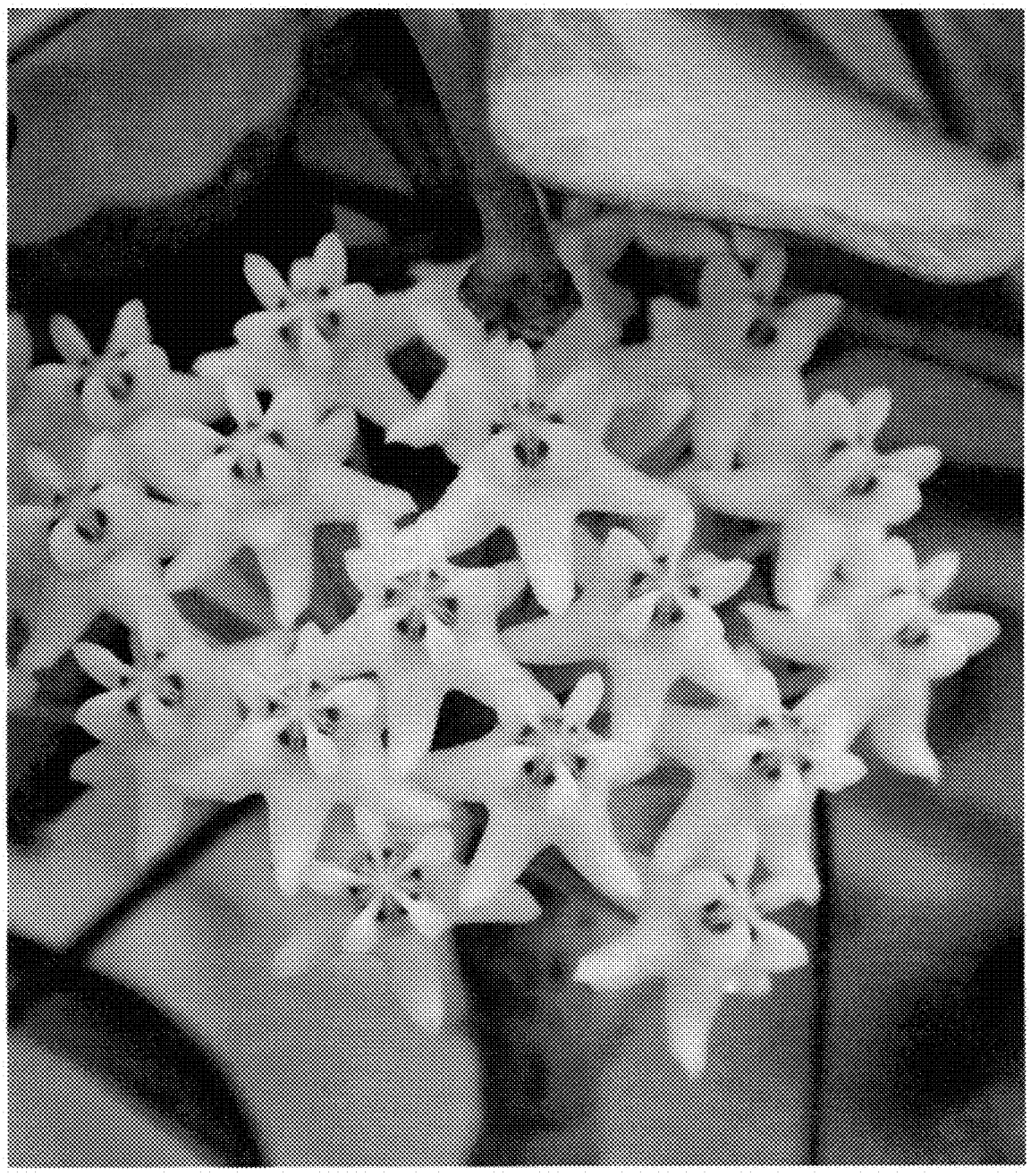
FIG. 3 illustrates, as nearly true as it is reasonably possible to make the same in color photographs of this type, the inflorescence of 'AMZ001'.

The following observations and measurements were made in January of 2024 and describe a 2-year-old 'AMZ001' plant grown in a 14 cm nursery pot grown in a greenhouse in Southwest Ranches, Florida. Plants were grown using conventional greenhouse production protocols for *Hoya* which consisted of growing under 70 percent shade with weekly manual irrigation and fertilizer applications as needed. No photoperiodic treatments or artificial light was given to the plants.

Those skilled in the art will appreciate that certain characteristics will vary with older or, conversely, with younger plants. 'AMZ001' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, third edition.

A botanical description of 'AMZ001' and comparisons with the parent and most similar commercial variety of *Hoya* are provided below.

Plant description:

*Growth habit*.—Evergreen vining perennial.

*Average height*.—Vining plant with indeterminate growth; approximately 60 cm as observed.

*Average width*.—Vining plant with indeterminate growth; approximately 25 cm as observed.

*Growth rate*.—Moderately fast growing.

*Plant vigor*.—Moderately vigorous.

*Propagation method*.—Softwood stem cuttings; rooting is initiated in approximately 14 days, and approximately 5 to 8 weeks are required to produce a rooted cutting when grown in a greenhouse with an ambient average temperature of 25 degrees Celsius.

*Time to produce a finished plant*.—Approximately 5 months are required to produce a fully rooted and marketable plant in a 7.5 cm nursery container, when grown under greenhouse conditions.

*Disease and pest resistance or susceptibility*.—Plants have not been observed to be susceptible or resistant to pathogens and pests common to *Hoya elliptica*.

*Environmental tolerances*.—Adapt to at least USDA Zones 10 through 12; moderate tolerance to rain; high tolerance to wind; low tolerance to drought.

Root system:

*General*.—Exhibits a relatively shallow root system with adventitious roots arising along the stems.

*Branching*.—Freely branched.

*Density*.—Moderately dense.

*Distribution*.—Relatively shallow.

*Texture*.—Fleshy; smooth; lacking root hairs.

Stem:

*Branching habit*.—Freely branching with scandent main stems and lateral branches.

*Number of main stems per plant*.—1.

*Number of lateral branches per plant*.—10.

*Aspect*.—Terete.

*Length of main stems*.—Indeterminate growth.

*Diameter of main stems*.—0.55 cm at the base.

*Internode length on main stems*.—Ranging from 3.0 to 7.0 cm; 5.1 cm average.

*Attitude*.—Vining; scadent.

*Strength*.—Weak.

*Texture and luster*.—Glabrous and matte.

*Color, juvenile*.—Yellow-green, RHS 145B, at the apex of juvenile stems; as juvenile stems mature, the color transitions to greyed-yellow, nearest to RHS 161D, and lightly to moderately suffused with greyed-red, nearest to RHS 178D.

*Color, mature*.—Greyed-yellow, nearest to RHS 161C, and becoming increasingly suffused with yellow-green towards the base of the plant, nearest to in between RHS 144A and 146A.

*Color at internodes*.—Greyed-yellow, nearest to RHS 161D, and lightly suffused with yellow-green, nearest to RHS 145B.

Foliage:

*Arrangement*.—Opposite decussate.

*Division*.—Simple.

*Attachment*.—Petiolate.

*Abundance*.—Very abundant; greater than 30 leaves per lateral branch.

*Lamina*.—Dimensions — 7.9 cm long and 3.4 cm wide, on average. Shape — Elliptic. Aspect — Near-flat. Apex — Broadly acute. Base — Acute. Margin — Entire; not undulated. Pubescence, texture and luster of adaxial surface — Glabrous, coriaceous, somewhat fleshy, and slightly glossy. Pubescence, texture and luster of abaxial surface — Glabrous, coriaceous, somewhat fleshy, and slightly glossy. Color — Juvenile foliage, adaxial surface — Yellow-green, nearest to RHS 144C; irregularly and narrowly margined with a darker shade of yellow-green, nearest to RHS 144A. Juvenile foliage, abaxial surface — Yellow-green, nearest to RHS 144C; irregularly and narrowly margined with a darker shade of yellow-green, nearest to RHS 144A. Mature foliage, adaxial surface — Yellow-green, nearest to RHS 145C; occasionally blotched with a darker shade of yellow-green towards the marginal zone, nearest to in between RHS 145A and 145B; irregularly and broadly margined green, nearest to RHS 137B. Mature foliage, abaxial surface — Yellow-green, nearest to RHS 145C; occasionally blotched with a darker shade of yellow-green towards the marginal zone, nearest to in between RHS 145A and 145B; irregularly and broadly margined green, nearest to RHS 137B. Venation — Pattern — Pinnate venation with brochidodromous secondary lateral veins. Venation color, adaxial surface — Yellow-green, nearest to RHS 150D. Venation color, abaxial surface — Yellow-green, nearest to RHS 150D.

*Petiole*.—Length — 1.3 cm. Width — 0.25 cm. Aspect — Subterete. Texture — Smooth and glabrous. Luster — Matte. Strength — Moderately strong. Color, juvenile foliage — Both the adaxial and abaxial surfaces are greyed-yellow, nearest to RHS 161D, and moderately suffused with greyed-red, nearest to RHS 178D. Color, mature foliage — The adaxial surface is greyed-yellow, nearest to RHS 161C, and lightly suffused with yellow-green, nearest to RHS 145B. The abaxial surface is greyed-yellow, nearest to RHS 161C, and lightly suffused with greyed-red, nearest to RHS 178D.

Inflorescence:

*Inflorescence type*.—Umbel.

*Natural flowering season*.—Late spring through summer in USA Hardiness Zone 11.

*Dimensions*.—Approximately 5.0 cm long, excluding peduncle, and 7.0 cm wide.

*Quantity of flowers per inflorescence*.—Approximately 20.

*Attitude*.—Upward.

*Peduncles*.—Length — Average of 1.4 cm. Diameter — Average of 0.35 cm. Attitude — Upward and outward. Strength — Moderately strong. Texture and luster — Smooth, glabrous and slightly glossy. Color — Yellow-green, a mixture of RHS 145A and 146C.

Bud:

*Shape*.—Globose; pentamerous.

*Dimensions*.—2.5 mm long and 2.0 mm in diameter.

*Color*.—Yellow-green, nearest to RHS 144C, and suffused with greyed-orange, RHS 175D, at the union of each segment.

*Texture*.—Smooth and glabrous.

*Luster*.—Slightly glossy.

Flower:

*Form*.—A five-lobed, stellate corolla topped by a five-lobed corona with lobes strongly curled inward, nearly touching at the center of the flower, and somewhat enveloping the star-shaped gynostegium.

*Attitude*.—Outward to upright.

*Lastingness*.—Approximately 7 days.

*Persistence*.—Not persistent; self-cleaning.

*Fragrance*.—Sweetly fragranced.

*Flower depth*.—1.9 cm.

*Flower diameter*.—1.4 cm.

*Corolla*.—Quantity of Petals — 5. Arrangement — Rotate with a single whorl of petals. Attitude of petal lobes — Reflexed. Shape of petal lobes — Narrowly deltoid. Aspect of petal lobes — Strongly revolute. Dimensions, free portion of petals — 0.65 cm long and 0.35 cm wide at the base of the free lobe. qjApex — Broadly acute. Base — Truncate; fused at the base. Margin — Entire and ciliate. Petal lobes are not undulated to very slightly undulating. Texture and luster of outer surface — Tomentose, waxy underneath, and matte. Corolla color when opening — White, nearest to RHS 155D, and suffused with yellow-green, RHS 145A. Corolla color when fully open — White, nearest to RHS 155D. No visible venation.

*Corona*.—Quantity of coronal lobes — 5. Arrangement — Rotate. Attitude of coronal lobes — Erect and strongly incurved, with the apices of each lobe nearly touching one another at the center of the flower. Shape of coronal lobes — Linear. Aspect of coronal lobes — Terete. Dimensions, free portion of coronal lobes — 0.7 cm long and 0.25 cm in diameter. Apex — Broadly acute. Base — Truncate; fused at the base. Margin — Entire. Texture and luster of outer surface — Waxy and glossy. Corolla — The fused base is red-purple, nearest to a combination of RHS 59A and 61A. The lobes are white, nearest to RHS 155D.

*Pedicels*.—Attitude — Upward and outward, at an average angle of 25 degrees to the peduncle; varying from 10 to 60 degrees. Dimensions — 3.3 cm long and 0.2 cm in diameter. Strength — Moderately strong. Texture and luster — Smooth, glabrous, and matte. Color — Greyed-red, nearest to RHS 182C.

*Calyx*.—Shape — Stellate; single whorl of sepals. Dimensions — 0.45 cm in diameter and 0.2 cm deep. Sepal lobes — Arrangement — Sepals are rotate and fused at the base. Quantity — 5.Shape — Deltoid. Dimensions — 2.5 mm long and 0.2 mm wide at the point of fusion. Apex — Acute. Base — Truncate; fused. Margin — Entire; not undulated. Pubescence, texture and luster, upper surface — Smooth; glabrous; matte. Color — Greyed-yellow, nearest to RHS 160B; apices of sepal lobes are suffused with greyed-red, RHS 182B.

Reproductive organs:

*General description*.—Specialized reproductive organs are fused into a gynostegium, with five fused pollinaria visible. The pollinaria are arranged in a stellate pattern.

*Dimensions*.—Approximately 0.3 cm high and 0.5 cm in diameter.

*Pollinaria color*.—Greyed-orange, nearest to RHS 167C; the point of fusion between pollinarium is translucent white, nearest to RHS 155D.

Seed and fruit: To date, seeds and fruit have not been observed.

COMPARISONS WITH THE PARENT PLANT

Plants of the new cultivar 'AMZ001' differ from the parent, an unnamed *Hoya elliptica* plant (not patented) by the characteristics described in Table 1.

TABLE 1

| Characteristic | 'AMZ001' | The parent |
|---|---|---|
| Rate of growth. | Slower growing than the parent. | Faster-growing than 'AMZ001'. |
| Expression of foliage variegation. | Pale yellow-green in the central zone and broadly margined with dark green. | No variegation; solid green. |

COMPARISON WITH THE MOST SIMILAR *HOYA* CULTIVAR KNOWN TO THE INVENTOR

There are no similar variegated antecedents of *Hoya elliptica* known to the inventor. There is, however, a cultivar of *Hoya camosa* named 'Krimson Princess' (not patented) that exhibits a similar foliar variegation pattern. Plants of the new cultivar 'AMZ001' differ from 'Krimson Princess' in the following characteristics described in Table 2 below.

TABLE 2

| Characteristic | 'AMZ001' | 'Krimson Princess' |
|---|---|---|
| Foliage aspect. | Flat. | Carinate; margins revolute. |
| General coloration of the corolla. | White. | Pink to red-purple. |
| Expression of foliage variegation. | Pale yellow-green in the central zone and broadly margined with dark green. | Irregularly centered with cream white, and broadly margined with mid-green. |

That which is claimed is:

1. A new and distinct *Hoya ellipitica* plant named 'AMZ001', substantially as described and illustrated herein.

* * * * *